United States Patent [19]

Allan

[11] Patent Number: 5,252,542
[45] Date of Patent: Oct. 12, 1993

[54] CONTROLLED RELEASE COMPOSITION AND METHOD FOR USING

[75] Inventor: George G. Allan, Seattle, Wash.

[73] Assignee: University of Washington, Seattle, Wash.

[21] Appl. No.: 686,015

[22] Filed: Apr. 12, 1991

Related U.S. Application Data

[63] Continuation of Ser. No. 266,247, Oct. 28, 1988, abandoned, which is a continuation of Ser. No. 868,664, May 29, 1986, abandoned, which is a continuation of Ser. No. 282,803, Jul. 13, 1981, abandoned.

[51] Int. Cl.$^5$ .................. A01N 37/10; A01N 37/38; B01J 13/02
[52] U.S. Cl. .................. 504/323; 71/DIG. 1; 264/4.6; 424/413; 424/461; 424/488; 427/213.36; 428/402.2; 428/402.24; 504/321; 512/4
[58] Field of Search ............. 264/4.6; 427/213.36; 428/402.2, 402.24; 71/DIG. 1; 424/413, 461, 488; 504/321, 323

[56] References Cited

U.S. PATENT DOCUMENTS

| | | | |
|---|---|---|---|
| Re. 29,238 | 5/1977 | Dimitri et al. | 71/DIG. 1 |
| 2,341,868 | 2/1944 | Hitchcock et al. | 71/114 |
| 3,871,906 | 3/1975 | Sweeny et al. | 71/DIG. 1 |
| 4,015,970 | 4/1977 | Hennart | 71/DIG. 1 |
| 4,055,974 | 11/1977 | Jackson, Jr. | 424/405 X |
| 4,087,273 | 5/1978 | Garrison et al. | 71/DIG. 1 |
| 4,111,684 | 9/1978 | Thomas et al. | 71/DIG. 1 |
| 4,172,714 | 10/1979 | Albert | 71/DIG. 1 |
| 4,244,728 | 1/1981 | Delli Colli et al. | 71/DIG. 1 |
| 4,388,352 | 6/1983 | Allan et al. | 424/413 X |

FOREIGN PATENT DOCUMENTS 46-42800 12/1971 Japan ................... 71/DIG. 1

OTHER PUBLICATIONS

Kistler,-36 J. Phys. Chem. 52 (1932).
Allan et al.: "Physical Entrapment, Etc.", (1970), Nature 225, pp. 175-176.
Balaban: "Cellulose Encapsulation and Controlled Release", Master of Science in Chem. Engineering Thesis, Placed on U. of Washington Shelf Sep. 20, 1981, Abstract pp. II-VIII and 43-49.
Allan et al.: "A New Simple Controlled Release Delivery System", Annals N.Y. Acad. Sci. 446: 14-25 (1985).

Primary Examiner—Richard D. Lovering
Attorney, Agent, or Firm—Seed and Berry

[57] ABSTRACT

Controlled release compositions are made by including chemical impregnants (such as animal repellants, pesticides, herbicides, fungicides, plant growth stimulants, perfumes, fertilizers, and drugs) in biodegradable, microporous structures. Each microporous structure collapses upon drying but swells upon rewetting to allow the impregnant entrapped in it to diffuse from the structure. Never-dried wood pulp is a particularly desirable microporous structure because it has large pores initially, a large surface area initially, and demonstrated swelling capability. Methods for making the novel controlled release compositions and methods of using the compositions are also disclosed.

32 Claims, 2 Drawing Sheets

CONTROLLED RELEASE COMPOSITION AND METHOD FOR USING

CROSS-REFERENCE TO RELATED APPLICATIONS

This application is a continuation of U.S. Ser. No. 07/266,247, filed Oct. 28, 1988, now abandoned; which is a continuation of U.S. Ser. No. 06/868,664, filed May 29, 1986, now abandoned; which is a continuation of U.S. Ser. No. 06/282,803, filed Jul. 13, 1981, now abandoned.

1. Technical Field

This invention relates to a novel controlled release composition, a method of use, and a method of manufacture. In particular, this invention relates to entrapping an impregnant in the pores of never-dried α-cellulose pulp before the pores collapse upon drying.

2. Background Art

Controlled release compositions are being recognized as the technology of the future to provide continuing activity over an extended period of time without the need for additional applications of the active agent. Controlled release compositions are useful with animal repellants, pesticides, herbicides, fungicides, plant growth stimulants, fertilizers, and drugs. Controlled release compositions allow application of a lesser amount of active agent to achieve better control than application of the active agent directly (which generally results in loss through leaching or otherwise before the active agent can be effectively used). Four mechanisms are commonly employed to obtain controlled release:

(1) desorption from strong sorbents, like silica gel, mica, and activated charcoal;
(2) diffusion;
(3) erosion of biodegradable barrier materials; and
(4) release after retrograde chemical reactions, such as hydrolysis, thermodynamic dissociation, or microbial degradation.

The delivery rate of a chemical from a controlled release system is primarily influenced by the architecture of the system, the properties of the compound included and the rate-controlling matrix, and the driving force liberating the compound from the matrix. Physical controlled release compositions are either reservoir systems or monolithic systems. In a reservoir system, the active agent is encapsulated within a rate-controlling membrane. The membrane permeability and the membrane configuration determine the release rate. In a monolithic system, the active agent is dissolved or dispersed throughout a matrix, such as a polymer.

One commercial reservoir system uses a hollow fiber to hold the active agent, such as an insect pheromone. The release of the active agent from the fiber is diffusion controlled. This system is beneficial for volatile liquids, yet it is expensive because of the cost of manufacture of the tubes. Many other controlled-release compositions are known, especially for insecticides, drugs, and fertilizers. Most are encapsulation reservoir systems similar to the hollow fibers but depending on diffusion through a semipermeable membrane.

When cellulose is swollen in water and the water is replaced by a solvent through a series of solvent exchanges, the final solvent is often entrapped inside the cellulose structure upon drying. The entrapped solvent is only released by contacting the cellulose with water. Kistler, 36 *J. Phys. Chem.* 52 (1932).

Because investigators have been interested primarily in enhancing the rates of chemical reactions by making inclusion cellulose, no systematic study of the inclusion process has been conducted. Believing that the solvents were entrapped in the amorphous or intercrystalline regions of the cellulose structure, most investigators thought that the molecular size of the solvents used must be small (less than about 10 angstroms). Blackwell, Kolpak, and Gardner, *Cellulose Chemistry and Technology*, 48 ACS Symp. Ser. 42 (1977). The release mechanism was thought to include destruction of the crystalline region of the cellulose during swelling. Small amounts of chemical solvents, such as ethylene glycol, methanol, ethanol, acetone, toluene, benzene, carbon tetrachloride, pyridine, n-hexane, chloroform, cyclohexane, isopropanol, n-butanol, bromobenzene, and dichloroethane, were released using water, ammonia, or sodium hydroxide as a swelling agent.

DISCLOSURE OF INVENTION

An economical controlled release composition of this invention comprises a carrier which entraps a bioactive impregnant, such as a plant growth stimulant, an herbicide, an animal repellant, a pesticide, a fungicide, a perfume or deodorizer, a drug, or a fertilizer. Initially, the carrier has a microporous structure into which a solution of impregnant flows, displacing fluid held in the pores of the structure. Upon drying, the pores of the carrier collapse to entrap the impregnant, reducing the largest effective pore radius from about 300 angstroms to about 25-50 angstroms. Upon wetting, the carrier swells, allowing the impregnant to diffuse out of the carrier. A desired biodegradable carrier is never-dried wood pulp of α-cellulose formed by dissolving lignin and hemicellulose out of wood fibers during the pulping process. This never-dried pulp has pores as large as 300 angstroms with a generally log normal pore size distribution. Initially, its surface area is about 1000 $m^2/g$; while, after drying, collapse, and rewetting, the surface area returns only to about 100 $m^2/g$.

The characteristic failure to recover fully upon swelling makes it important that the impregnant enter the carrier before it is dried. The controlled release compositions of this invention are best distinguished over prior cellulose inclusion compounds in that the impregnant is inserted into the carrier before drying of the carrier. Before drying, the pores of the carrier are as large as possible so that diffusion of the impregnant into the carrier is least restricted. Upon collapse, impregnant is trapped in some pores where impregnant could not reach if diffused into "once-dried" carrier. Thus the use of a carrier which has initially uncollapsed pores allows for better entrapment of impregnant and better controlled release.

To slow the diffusional release of impregnant, the carrier may be treated with a biodegradable, film-forming polymer coating, such as polyvinyl alcohol, polyvinyl acetate, polyethylene glycol, or mixtures thereof. The polymer coating delays the swelling of the carrier upon rewetting by shielding the cellulose lamellae from the swelling liquid. The pores open more slowly, delaying the diffusion of impregnant from the carrier. Alternatively, control of the release rate can be obtained by forming the impregnated pulp into tablets, mats, sheets, or the like.

BEST MODE FOR CARRYING OUT THE INVENTION

Figure 1:
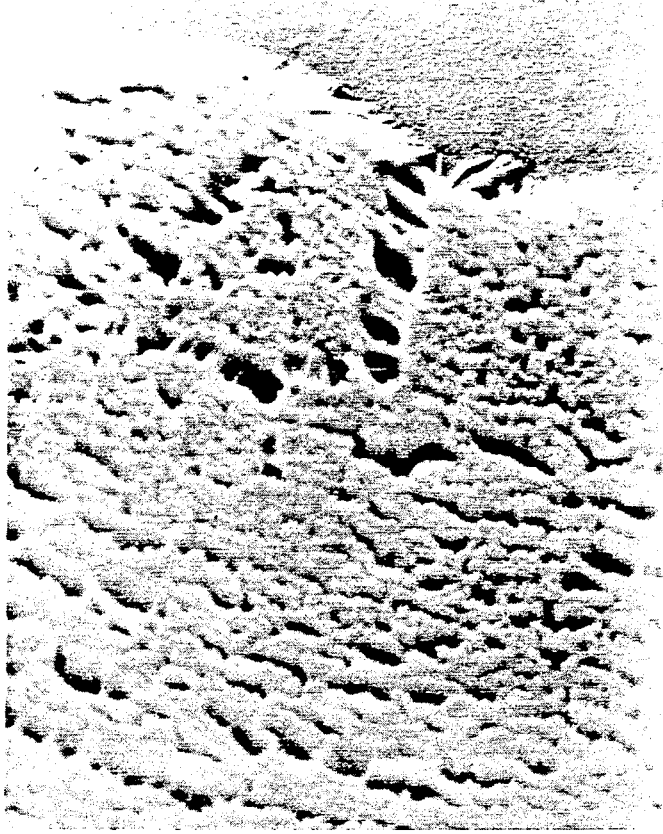
FIG. 1 is a photomicrograph of never-dried wood pulp.
Figure 2:
FIG. 2 is a photomicrograph of wood pulp, dried and rewet.

FIGS. 1 and 2 show the marked difference in structure between never-dried wood pulp and wood pulp; dried and rewet. The never-dried pulp has much larger lamellar pores. This invention capitalizes on the structural difference in the pulp to prepare an improved controlled release composition.

Figure 3:
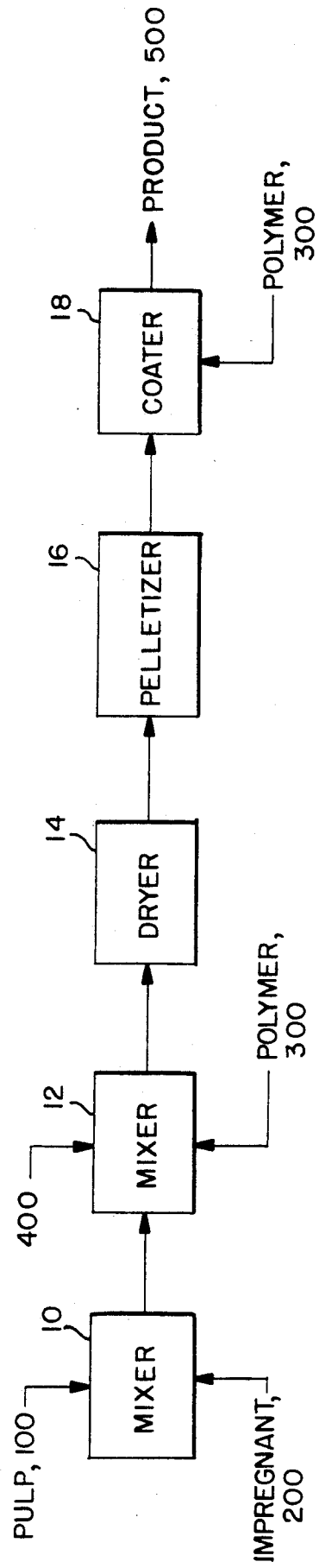
FIG. 3 is a schematic flow diagram showing a method of making a controlled release composition.

FIG. 3 is a schematic flow diagram for a method of making a controlled release composition. Never-dried sulfite wood pulp 100 having a 60% moisture content (gm $H_2O$/100 gm wet pulp) is mixed in a mixer 10 with a solution 200 of impregnant so that the moisture in the pulp exchanges with the solution. The treated pulp passes into a second mixer 12 where a polymer coating 300 of polyvinyl alcohol, polyvinyl acetate, polyethylene glycol, other water-degradable polymers, or mixtures thereof may be added to the pulp. A polymer coating slows release of the impregnant because of the presence of an additional diffusion barrier. Alternatively to applying a polymer coating in this second mixer 12, a precipitating liquid or solution 400, such as solutions of phosphoric acid or hydrochloric acid, may be added so that the precipitate impregnant will better remain in the pores of the α-cellulose pulp. Passing from the mixer 12 into a dryer 14, the treating solutions are withdrawn under suction and the pulp is dried. Once dry, the pulp is formed into tablets, mats, sheets, or the like in a pelletizer 16, and is coated with a polymer 300 in the coater 18 to yield the final product 500. The controlled release compositions of this invention are easy to make from economical components. They are useful for a wide variety of applications, including release of plant growth stimulants (such as 2,4-dichlorophenoxyacetic acid or naphthaleneacetic acid); herbicides (such as higher concentrations of 2,4-dichlorophenoxyacetic acid or naphthaleneacetic acid); pesticides; fungicides; perfumes, deodorizers, and ammonia scavengers (such as citric acid); animal repellants (such as methyl nonyl ketone); drugs (such as aspirin); fertilizers (such as commercially available phosphate and nitrogen compounds); and the like. When never-dried wood pulp is used as the carrier for an impregnant of this type, release is diffusion controlled with a pseudo first-order rate constant. Those skilled in the art will recognize that multiple stages of solvent exchange, drying, or coating may be used, if desired.

Never-dried pulp is formed by removing the lignin and hemicellulose from wood fibers during pulping by any of the well-recognized pulping processes. The pulp obtained is a composite of several hundred concentric lamellae of cellulose microfibrils. Each lamella is separated from the others by water-filled spaces (pores) which vary in width from about 25–300 angstroms. The larger spaces are located nearer the periphery, with the narrower toward the lumen (a central channel of about 10–20 μ width). The spacing more or less corresponds to the thickness of the lignin in the wood fiber. The pore size forms a generally log normal distribution; that is, a plot of the logarithm of the pore size against frequency has a generally Gaussian distribution. The never-dried pulp has a surface area of about 1000 $m^2/g$. Upon drying, the surface area reduces to about 1 $m^2/g$. Even though the lamellae swell upon rewetting, the rewetted pulp has a surface area of only about 100 $m^2/g$. Thus, upon drying, the pores of the never-dried pulp irreversibly collapse. This invention capitalizes on the collapse as a way to trap impregnant in the pulp so that its release will be controlled. It also uses never-dried pulp for faster diffusion of larger chemicals into the microporous structure of the cellulose.

At least five ways are known to reduce pore collapse at the encapsulation stage (i.e., diffusion of impregnant into the pores). First, the capillary pressure forces can be decreased by reducing interfacial tensions. The interfacial tensions, in turn, may be reduced by use of a surface active material (surfactant), by use of a liquid which develops low interfacial tensions, or by increase of the encapsulation temperature. The capillary pressure forces may be completely eliminated if the solution for encapsulation is miscible with the previous solvent remaining within the cell wall pores. Second, the electrical repulsive forces may be increased by use of materials like anionic surfactants which may increase the surface charge density by being specifically adsorbed onto cellulose structure. Third, the long-range van der Waals attractive forces may be decreased by selecting, when possible, a solvent which minimizes the values of the Hamaker constant between the lamellae and liquid medium. (See, e.g., P. HIEMENZ, PRINCIPLES OF COLLOID AND SURFACE CHEMISTRY, Marcel-Dekker (1977) 412–418.) Fourth, the use of a swelling agent more powerful than water, such as liquid ammonia, formamide, or an aqueous alkaline or acidic solution, will produce more pores in the cell walls. Fifth, steric hindrance may be used to prevent collapse by incorporating bulky molecules into the pores.

The never-dried pulp is immersed in a solution of impregnant, such as 2,4-dichlorophenoxyacetic acid, naphthaleneacetic acid, methyl nonyl ketone, aspirin, diethyl toluamide, selenium dioxide (in water or ethyl alcohol), or the like. Chemicals as large as about 300 angstroms may be used as impregnants for never-dried wood pulp (this dimension being substantially equal to the largest pore). Much larger molecules may be used as impregnants with never-dried pulp than with "once-dried" pulp. Therefore, never-dried pulp presents opportunities for much greater use.

The solution of impregnant diffuses through the pulp to displace water otherwise in the pores. Another liquid is used to wash and to cool the pulp after the solution has exchanged with the water. This second liquid, such as a cold water or dilute acid wash, causes the impregnant to crystallize and to precipitate in the pores so that more impregnant will remain in the pulp upon drying. The pulp is then dried to form the controlled release composition. Ordinarily, the impregnated pulp is formed into mats, sheets, tablets, or the like to allow easier handling and to provide further control of the release. Often a polymer coating is added to the tablets as yet another means to control the rate.

When the solution of impregnant is immiscible in water, solvent exchange steps can be avoided by using a distillation method to include the impregnant into the carrier. The never-dried pulp is directly mixed with the water-immiscible solvent, such as n-hexane or toluene, in a reactor. The mixture is heated to evaporate the water and solvent, which are condensed and collected in a distilling receiver. If required to remove all the water from the reactor, additional solvent is added to the reactor. Solvent can be recycled from the distilling receiver. In other details, this method follows the steps already described.

In selecting a solvent for the distillation method just described, four factors should be considered. First, a solvent with a higher boiling point is more effective in eliminating water from the pulp. Second, the lower the interfacial tension between the water in the pulp and the solvent, the smaller are the contracting forces developed within the cell pores. Third, the more a solvent reduces the attractive forces (i.e., long-range van der Waals forces) within the cell wall pores, the better the solvent is. Fourth, the higher the surface tension of the solvent, the greater the amount of impregnant trapped when the cell walls collapse upon drying. For example, suitable solvents are toluene, xylene, and other aromatic hydrocarbons; n-hexane, n-octane, and other lower aliphatic or cyclic hydrocarbons; ethyl acetate and other esters; carbon tetrachloride and other chlorinated solvents; diethyl ether and other ethers; and ethyl alcohol and other lower aliphatic alcohols.

A surfactant may be added to the reactor mixture to enhance the inclusion of impregnant into the cellulose pulp. A suitable surfactant should be soluble in the water and solvent over a wide range of temperatures. It should be stable at high temperatures without sublimation or evaporation.

Because the reactor is operated at the boiling point of the mixture, the solubility of the solute in the mixture can be increased greatly. As the solvent and water are distilled off, the solute concentration rises, increasing the inclusion amount entrapped in the pores. Because the pulp is always immersed in solution throughout the inclusion process, the chances of early pore collapse are diminished in comparison with conventional solvent exchange steps which alternate immersions with filtrations as the solvents are changed in a number of stages. Finally, the distillation method reduces the number of steps ordinarily required in conventional solvent exchange. Thus the distillation method is superior to solvent exchange when the solvent and water are immiscible.

Although broadly applicable to a variety of controlled release compositions, this invention is probably best understood with reference to the following examples.

I. METHODS FOR PREPARING CONTROLLED RELEASE COMPOSITIONS CONTAINING 2,4-DICHLOROPHENOXYACETIC ACID

Useful as a plant growth stimulant at lower dosage levels and as an herbicide at higher dosage levels, 2,4-dichlorophenoxyacetic acid has been widely studied. Six methods for including it in an $\alpha$-cellulose pulp, controlled release composition are:

EXAMPLE 1

Two grams of 2,4-dichlorophenoxyacetic acid were dissolved in 25% $NH_4OH$ solution (60 ml). Three grams of never-dried sulfite pulp were immersed in the solution for 25 minutes. (During immersion, the solution was mixed occasionally.) The pulp was filtered under reduced pressure and immersed in 60 ml of 10% phosphoric acid for 3 minutes. Again the pulp was filtered and the filter cake was washed with ice water until the filtrate pH was 6.8. Thereafter, the filter cake was oven dried at 75° C. (Other amounts of 2,4-dichlorophenoxyacetic acid may be used to vary the concentration of impregnant in the pulp.)

EXAMPLE 2

Three grams of never-dried sulfite pulp were soaked in 35% ethanol (100 ml) for 2 hours at room temperature for solvent exchange with water in the pulp, then filtered under reduced pressure. The pulp was placed in an ethanol solution (100 ml) of 2,4-dichlorophenoxyacetic acid (5 g) for 25 minutes. The sample was mixed a few times during that period and filtered under reduced pressure to obtain a wet pulp mat. This mat was air dried.

EXAMPLE 3

The method of Example 2 was followed, except that, prior to drying, the wet pulp was washed with ice water (50 ml) for 30 seconds to precipitate the impregnant in the pores and filtered. Then the sample was oven dried at 75° C.

EXAMPLE 4

The method of Example 2 was followed, except that, prior to air drying, a 5% solution of polyvinyl alcohol in water was brushed on both sides of the wet pulp mat.

EXAMPLE 5

The method of Example 1 was followed to make six mats. Each mat was then coated with one of six polymer solutions:

(1) 1% polyvinyl alcohol in water;
(2) 2% polyvinyl alcohol in water;
(3) 11% polyvinyl acetate in water;
(4) 18% polyvinyl acetate latex in water;
(5) 33% polyvinyl acetate latex in water;
(6) 33% aqueous solution of polyvinyl acetate latex and polyethylene glycol (2 g polyvinyl acetate/1 g polyethylene glycol)

EXAMPLE 6

Three grams of never-dried sulfite pulp were immersed in a solution of 100 ml toluene, eight grams of 2,4-dichlorophenoxyacetic acid, 10 ml water, and 0.02% of the surfactant Brij (polyoxyethylene (23) lauryl ether). The solution was distilled in a Dean-Stark distilling receiver until all water was removed. The pulp was filtered and air dried. The dried mat was washed with tetrahydrofuran until all the 2,4-dichlorophenoxyacetic acid was washed from the surface.

All methods produced a pulp mat suitable for use as a controlled release composition. Those with polymer coatings had release rates slower than that of 2,4-dichlorophenoxyacetic crystals or mats which were not coated with polymer.

II. METHODS FOR PREPARING CONTROLLED RELEASED COMPOSITIONS CONTAINING NAPHTHALENEACETIC ACID

As with the mats prepared containing 2,4-dichlorophenoxyacetic acid, mats containing naphthaleneacetic acid have been found to be useful as a time-release herbicide. Four methods for preparation of these mats are:

EXAMPLE 7

Four grams of naphthaleneacetic acid were dissolved in 25% $NH_4OH$ solution (60 ml). Three grams of never-dried pulp were immersed in this solution for 25 minutes. The pulp was stirred occasionally and was filtered under reduced pressure. In other details, the method was the same as that of Example 1.

EXAMPLE 8

Three grams of never-dried sulfite pulp were immersed for 2 hours in 60 ml of tetrahydrofuran. The pulp was filtered under reduced pressure. The filter cake was then immersed in a solution of four grams of napthaleneacetic acid in 60 ml of tetrahydrofuran. After 1 hour, the pulp was filtered and air dried.

EXAMPLE 9

Solvent exchange between the never-dried pulp and a solution of naphthaleneacetic acid was used with four other solutes:
(1) ethanol;
(2) dioxane;
(3) diethyl ether; and
(4) acetone.
Otherwise, the method of Example 8 was followed.

EXAMPLE 10

The method of Example 6 was used, except that five grams of naphthaleneacetic acid replaced the eight grams of 2,4-dichlorophenoxyacetic acid.

All mats were be used as controlled release compositions for naphthaleneacetic acid. Other concentrations of naphthaleneacetic acid in the pulp may be used with the consequent changes in the amount of acid which diffuses into the carrier and in the diffusion rate.

III. METHODS FOR PREPARING CONTROLLED RELEASE COMPOSITIONS CONTAINING ASPIRIN

To illustrate the controlled release of drugs and to test the added control of tablets, the following tests with never-dried pulp and aspirin were conducted.

EXAMPLE 11

Five grams of never-dried pulp were immersed in 100 ml of ethanol for 3 minutes. The pulp was filtered and added to a saturated solution of aspirin (75 g) in ethanol (100 ml). After 5 minutes of stirring, the pulp was recovered by filtering under suction. The filter cake was dried at 50° C. under reduced pressure for 24 hours.

EXAMPLE 12

The method of Example 11 was used, but the initial step of solvent exchange between the pulp and ethanol was eliminated.

More aspirin was found in the controlled release composition made in Example 12, presumably because the solvent exchange facilitates the diffusion of the aspirin into and out of the pulp, leading to greater losses from the inclusion compound on drying. Alternatively, the solvent exchange method may cause dilution of the aspirin solution, leading to a lower equilibrium value. In both cases (i.e., with or without solvent exchange), the product likely held an excessive amount of aspirin over the theoretical inclusion value within the cell wall based on the total accessible pore volume (1.25 ml/g) and the density of the aspirin solution (0.95 g/ml). Thus, aspirin was apparently trapped between lamellae that collapsed rather than merely being found in pores in the cellulose layers.

EXAMPLE 13

Tablets were made from the products of Examples 11 and 12 by passing the products through a 9/16-inch concave die at a compression load of 1000 pounds. Each tablet contained 650 mg aspirin. Tests of the release rate were conducted to verify that the tablets slowed the diffusion process. While the filter cake products made by the methods of Examples 11 and 12 had half-lives of about 25 hours, tablets from these products had half-lives of about 215 hours. These tests indicate that pelletizing can be an important step in formulating a controlled release composition which will release small dosages of drugs over an extended period of time.

IV. TESTS OF CONTROLLED RELEASE AS A PLANT GROWTH STIMULANT OR HERBICIDE

To verify that either 2,4-dichlorophenoxyacetic acid or naphthaleneacetic acid could be used as a controlled release composition in farming, tests were run to determine the sensitivity of cucumbers to varying amounts of these drugs.

EXAMPLE 14

Mats of naphthaleneacetic acid in never-dried pulp were formed using the method of Example 1. Each mat was washed with tetrahydrofuran to form a test product having 20% naphthaleneacetic acid by weight on a dry pulp basis.

Between 5-50 mg (in increments of 5 mg) of mat material were spread on the surface of soil in a planting cup containing cucumber seeds. A little soil was sprinkled over the mat material, and 5 ml of water were added to each planting cup each day.

The plants were kept until flowering, when the number of leaves and flowers was counted and the height of each plant was measured. Finally, the plants were separated from the soil, washed, and dried for measurement of the dry weight.

At a dosage of 5 mg, the cucumber plants reached their maximum height, maximum root length, and maximum weight. Above 30 mg, the cucumber plants died. Growth declined from a maximum at 5 mg as larger dosages were applied.

EXAMPLE 15

Mats of 2,4-dichlorophenoxyacetic acid in never-dried pulp were formed using the method of Example 1. Each mat was washed with tetrahydrofuran to form a test product having 20% 2,4-dichlorophenoxyacetic acid by weight on a dry pulp basis.

In planting cups containing cucumber seeds, between 10 mg and 150 mg (in 10 mg increments) of mat material were spread on the surface of the soil. A little soil was sprinkled over the mat material, and 5 ml of water were added to each planting cup each day.

The plants were kept until flowering, when the number of flowers and leaves was counted and the height of each plant was measured. Finally, the plants were separated from the soil, washed, and dried for measurement of the dry weight.

Maximum growth was found at the 20 mg dosage level. Above about a 40 mg dosage level, growth was inhibited. At the 60 mg dosage level, no growth was observed. Thus, at low dosage levels, 2,4-dichlorophenoxyacetic acid stimulated plant growth, while at high dosage levels, the acid acted as an herbicide.

EXAMPLE 16

To test the herbicidal activity at dosage levels above 60 mg. new cucumber seeds were planted each week. Herbicidal activity continued for 40 days. When the activity finally declined, the growth of the seedlings was stimulated by the lower level of 2,4-dichlorophenoxyacetic acid then present in the soil.

I claim:

1. A controlled release plant-growth stimulant composition comprising a never-dried cellulose pulp carrier having a multilamellar cellulose structure and a plant-growth stimulant impregnant, wherein the impregnant is trapped within the never-dried cellulose carrier.

2. The controlled release plant-growth stimulant composition of claim 1 wherein the impregnant is 2,4-dichlorophenoxyacetic acid.

3. The controlled release plant-growth stimulant composition of claim 1 wherein the impregnant is naphthaleneacetic acid.

4. The controlled release plant-growth stimulant composition of claim 1, further comprising a biodegradable polymer coating.

5. The controlled release plant-growth stimulant composition of claim 4 wherein the biodegradable polymer coating is selected from the group consisting of polyvinyl acetate, polyvinyl alcohol and a mixture of polyvinyl acetate and polyethylene glycol.

6. A controlled release herbicide composition comprising a never-dried cellulose pulp carrier having a multilamellar cellulose structure and a herbicide impregnant, wherein the impregnant is trapped within the never-dried cellulose carrier.

7. The controlled release herbicide composition of claim 6 wherein the impregnant is 2,4-dichlorophenoxyacetic acid.

8. The controlled release herbicide composition of claim 6 wherein the impregnant is naphthaleneacetic acid.

9. A controlled release composition comprising a never-dried cellulose pulp carrier having a multilamellar cellulose structure and 2,4-dichlorophenoxyacetic acid, wherein the 2,4-dichlorophenoxyacetic acid is trapped within the never-dried cellulose carrier.

10. A controlled release composition comprising a never-dried cellulose pulp carrier having a multilamellar cellulose structure and naphthaleneacetic acid, wherein the naphthaleneacetic acid is trapped within the never-dried cellulose carrier.

11. The controlled release composition of claim 10 wherein the biodegradable polymer coating is selected from the group consisting of polyvinyl acetate, polyvinyl alcohol and a mixture of polyvinyl acetate and polyethylene glycol.

12. A controlled release composition comprising a never-dry pulp carrier having a multilamellar cellulose structure and naphthaleneacetic acid, wherein the naphthaleneacetic acid is trapped within the never-dry cellulose carrier.

13. The controlled release composition of claim 12 further comprising a biodegradable polymer coating.

14. The controlled release composition of claim 13 wherein the biodegradable polymer coating is selected from the group consisting of polyvinyl acetate, polyvinyl alcohol, and a mixture of polyvinyl acetate and polyethylene glycol.

15. A composition of matter comprising a multiplicity of never-dry cellulose lamellae each separated at least in part by a layer of a chemical forming a multilamellar structure, wherein the structure collapses upon drying to entrap the chemical therein and partially swells upon rewetting to allow the chemical to diffuse from the structure, and wherein the chemical is plant growth stimulant.

16. The composition of matter of claim 15 wherein the chemical is 2,4-dichlorophenoxyacetic acid.

17. The composition of matter of claim 15 wherein the chemical is napthaleneacetic acid.

18. The composition of matter of claim 15, additionally comprising a biodegradable polymer coating forming a film around the multilamellar structure.

19. The composition of matter of claim 18 wherein the polymer coating is polyvinyl acetate.

20. The composition of matter of claim 18 wherein the polymer coating is polyvinyl alcohol.

21. The composition of matter of claim 18 wherein the polymer coating is a mixture of polyvinyl acetate and polyethylene glycol.

22. A composition of matter comprising a multiplicity of never-dry cellulose lamellae each separated at least in part by a layer of a chemical forming a multilamellar structure, wherein the structure collapses upon drying to entrap the chemical therein and partially swells upon rewetting to allow the chemical to diffuse from the structure, and wherein the chemical is a herbicide.

23. The composition of matter of claim 22 wherein the chemical is 2,4-dichlorophenoxyacetic acid in concentrations effective as a herbicide.

24. The composition of matter of claim 22 wherein the chemical is napthaleneacetic acid in concentrations effective as a herbicide.

25. The composition of matter of claim 22, additionally comprising a biodegradable polymer coating forming a film around the multilamellar structure.

26. The composition of matter of claim 25 wherein the polymer coating is polyvinyl acetate.

27. The composition of matter of claim 25 wherein the polymer coating is polyvinyl alcohol.

28. The composition of matter of claim 25 wherein the polymer coating is a mixture of polyvinyl acetate and polyethylene glycol.

29. A method for the controlled release of the plant growth stimulant from the multilamellar structure of claim 15, comprising the steps of:
  (a) delivering an effective amount of the multilamellar structure containing the plant growth stimulant to a treatment area;
  (b) wetting the multilamellar structure, causing it to swell; and
  (c) allowing the plant growth stimulant to diffuse out of the swollen multilamellar structure.

30. A method for the controlled release of the plant growth stimulant from the multilamellar structure of claim 18, comprising the steps of:
  (a) delivering an effective amount of the multilamellar structure containing the plant growth stimulant to a treatment area;
  (b) degrading at least a part of the polymer coating;
  (c) wetting the multilamellar structure, causing it to swell; and
  (d) allowing the plant growth stimulant to diffuse out of the swollen multilamellar structure.

31. A method for the controlled release of the herbicide from the multilamellar structure of claim 22, comprising the steps of:

(a) delivering an effective amount of the multilamellar structure containing the herbicide to a treatment area;

(b) wetting the multilamellar structure, causing it to swell; and (c) allowing the herbicide to diffuse out of the swollen multilamellar structure.

32. A method for the controlled release of the herbicide from the multilamellar structure of claim 25 comprising the steps of:
(a) delivering an effective amount of the multilamellar structure containing the herbicide to a treatment area;
(b) degrading at least a part of the polymer coating;
(c) wetting the multilamellar structure, causing it to swell; and
(d) allowing the herbicide to diffuse out of the swollen multilamellar structure.

* * * * *